United States Patent
Castro

(10) Patent No.: US 11,419,654 B2
(45) Date of Patent: Aug. 23, 2022

(54) SURGICAL FASTENER

(71) Applicant: Blue Sky Technologies, LLC, Louisville, KY (US)

(72) Inventor: Frank Castro, Louisville, KY (US)

(73) Assignee: BLUE SKY TECHNOLOGIES, LLC

( * ) Notice: Subject to any disclaimer, the term of this patent is extended or adjusted under 35 U.S.C. 154(b) by 0 days.

(21) Appl. No.: 16/807,239

(22) Filed: Mar. 3, 2020

(65) Prior Publication Data

US 2020/0197061 A1 Jun. 25, 2020

Related U.S. Application Data

(63) Continuation of application No. PCT/US2019/038656, filed on Jun. 24, 2019.

(60) Provisional application No. 62/722,229, filed on Aug. 24, 2018.

(51) Int. Cl.
*A61B 17/86* (2006.01)

(52) U.S. Cl.
CPC .......... *A61B 17/864* (2013.01); *A61B 17/863* (2013.01); *A61B 17/8605* (2013.01); *A61B 17/866* (2013.01); *A61B 17/8625* (2013.01)

(58) Field of Classification Search
CPC .............................. A61B 17/864; A61B 17/869
See application file for complete search history.

(56) References Cited

U.S. PATENT DOCUMENTS

| | | | | |
|---|---|---|---|---|
| 4,537,185 A * | 8/1985 | Stednitz | ............. | A61B 17/8635 606/304 |
| 4,961,740 A * | 10/1990 | Ray | ....... | A61F 2/4611 606/279 |
| 5,096,352 A | 3/1992 | Lemelson | | |
| 5,658,285 A * | 8/1997 | Marnay | .................... | A61F 2/446 606/76 |
| 6,048,343 A | 4/2000 | Mathis et al. | | |
| 6,224,631 B1 * | 5/2001 | Kohrs | ..................... | A61F 2/446 623/17.11 |
| 9,526,547 B2 * | 12/2016 | Reed | ..................... | A61B 17/864 |
| 9,770,277 B2 * | 9/2017 | Biedermann | ........ | A61B 17/864 |
| 9,848,892 B2 | 12/2017 | Biedermann et al. | | |
| 9,943,340 B2 | 4/2018 | Whipple et al. | | |
| 2005/0021084 A1 * | 1/2005 | Lu | ........................ | A61B 17/864 606/218 |
| 2005/0184121 A1 | 8/2005 | Heinrich | | |
| 2006/0100627 A1 * | 5/2006 | Stone | .................... | A61F 2/0805 606/907 |
| 2006/0142772 A1 | 6/2006 | Ralph et al. | | |
| 2006/0276788 A1 | 12/2006 | Berry et al. | | |
| 2007/0055244 A1 * | 3/2007 | Jackson | ............. | A61B 17/8625 606/86 A |
| 2008/0154314 A1 | 6/2008 | McDevitt | | |
| 2008/0177331 A1 | 7/2008 | Perez-Cruet et al. | | |
| 2010/0298889 A1 | 11/2010 | Wilberg et al. | | |
| 2012/0041395 A1 * | 2/2012 | Sweeney | ............ | A61B 17/7061 606/313 |
| 2012/0046698 A1 | 2/2012 | Kolb et al. | | |
| 2012/0323285 A1 | 12/2012 | Assell et al. | | |

(Continued)

*Primary Examiner* — Nicholas W Woodall
(74) *Attorney, Agent, or Firm* — Business Patent Law, PLLC

(57) ABSTRACT

The present invention is a fastener (30). The current fastener (30) is particularly useful in surgical procedures. Among other things, the surgical fastener (30) is provided with a conduit (50, 210) to dispense or carry biocompatible substances.

19 Claims, 8 Drawing Sheets

(56) References Cited

U.S. PATENT DOCUMENTS

| | | |
|---|---|---|
| 2013/0041412 A1 | 2/2013 | Moumene |
| 2013/0310883 A1 | 11/2013 | Levy et al. |
| 2014/0303676 A1 | 10/2014 | Stronecek et al. |
| 2016/0000489 A1 | 1/2016 | Kaloostian |
| 2017/0227039 A1 | 8/2017 | Shih |

* cited by examiner

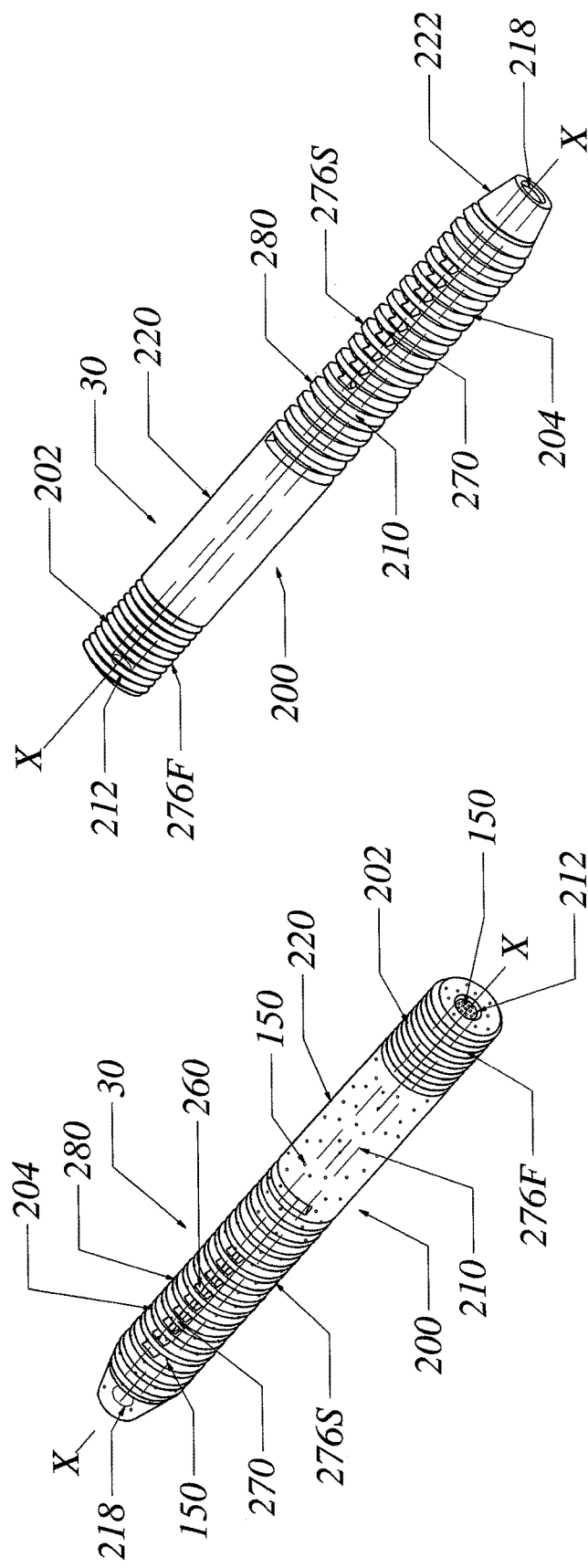
Fig. 11
Fig. 12
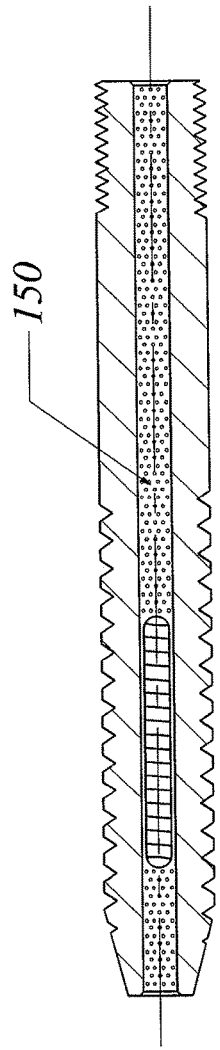
Fig. 11a

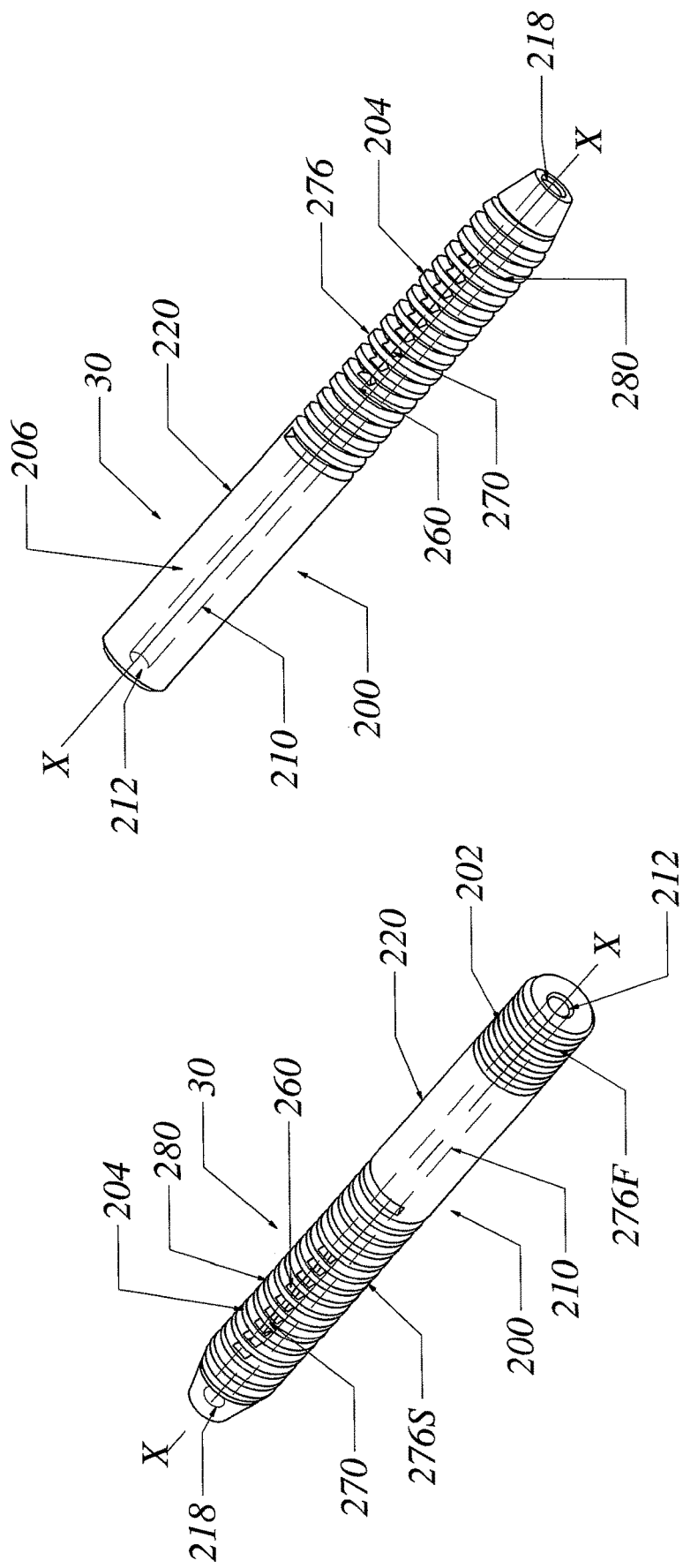

SURGICAL FASTENER

PRIORITY

Applicant claims priority to PCT US 2019/038656—Surgical Fastener—filed on Jun. 24, 2019 that claims the benefit of U.S. Provisional Application No. 62/722,229—Surgical Fastener—filed on Aug. 24, 2018.

BACKGROUND OF THE INVENTION

A. Field of the Invention

Among other things, the present invention is a fastener adapted for insertion into bone or any other tissue capable of interlocking with the thread or threads of the fastener. The fastener is provided with a conduit for transporting biocompatible devices/substances. Preferred embodiments the current fastener can include a standard or polyaxial head attached to the shank or a cannula with no head.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references. References that may indicate a state-of-the-art for the current invention include 1) U.S. Pat. No. 6,048,343—Mathis, et al.; 2) U.S. Pat. No. 9,848,892—Biedermann, et al. 3) US Published Patent Application No. 20060276788—Berry, et al.; 4) US Patent Application No. 20120046698—Kolb, et al.; 5) US Published Patent Application No. 20100298889—Wilberg, et al.; 6) US Published Patent No. 20060142772—Ralph, et al.; 7) U.S. Pat. No. 9,943,340—Whipple, et al.; 8) U.S. Pat. No. 5,096,352-Lemelson; 9) US Patent Application No. 20080177331—Perex-Cruet, et al.; 10) US Patent Application No. 20130041412—Moumene; 11) US Patent Application No. 20170227039—Shih; and 12) US Patent Application No. 201320310883—Levy, et al.

Among other things, the above references do not disclose a shank for a surgical fastener; the shank comprising: a) a longitudinal axis traversing from a first end to a second end opposite the first end; b) a conduit extending between the first end and the second end; the conduit adapted to carry one or more biocompatible substances; c) an inward side contiguous with the conduit and an outward side integral with the inward side; d) openings positioned between the first end and the second end; each opening extending through the inward and outward sides, wherein an outward edge of each opening corresponds to the radius of the outward side such that each opening is adapted to dispense biocompatible substances into a surgical environment external of the shank; and e) a thread attached to the outward side and turning through a second radius outward from the radius of the outward side, wherein at least a first wind of the thread circumscribes each opening.

Among other things, the above references do not disclose a surgical fastener comprising a cannula; the cannula comprising: a) an inward conduit adapted to carry one or more biocompatible substances; the conduit traversing a longitudinal axis of the cannula; b) a wall surrounding the conduit comprising: a first thread zone positioned at a first end of the cannula and a second thread zone positioned at a second end of the cannula; c) openings positioned in the second thread zone; each opening extending from the conduit through the wall such that each opening opens to a surgical environment external of the cannula, wherein an outward edge of each opening corresponds to a first radius; d) a first thread turning about the first thread zone; and e) a second thread positioned in the second thread zone and spiraling through a second radius more distant from the longitudinal axis than the first radius, wherein at least a first wind of the thread circumscribes each opening.

SUMMARY OF THE INVENTION

The present invention provides a biocompatible fastener that can be inserted into tissues that can interlock with one or more of the fastener's threads. Preferred embodiments of the current fastener can be utilized for transporting biocompatible devices/substances, such as adhesives, cannulas, fiber optics, implants, pharmaceuticals, osteogenic substances, etc. Preferred embodiments of the fastener's shank or cannula are provided with one or more openings lateral from the conduit. The openings can assist tissue growth, such as bone, into and through the fastener as well onto the inward surfaces of the fastener.

An aspect of the present invention is to provide a shank or cannula with one or more openings.

Still another aspect of the present invention is to provide a first radius from the longitudinal axis of the shank or cannula where one or more openings in the surgical fastener can coincide with the first radius.

It is still another aspect of the present invention to provide openings of one or more dimensions.

Yet still another aspect of the present invention is to provide one or more threads including winds that turn about a second radius from the longitudinal axis of the shank where the second radius is outward from the first radius.

Still another aspect of the present invention is to provide a shank or cannula where at least one thread includes a wind that circumscribes at least one opening.

Yet another aspect of the present invention is to provide a shank where surface treatments were applied to at least some portions of shank or cannula.

It is still another aspect of the present invention to provide a cannula that includes first and second thread zones, where the first thread and the second thread have distinct pitches.

Still another aspect of the present invention is to provide a surgical fastener that is adapted to facilitate tissue or bone growth.

Yet still another aspect of the present invention is to provide a surgical fastener with one or more threads that include one or more winds that circumscribe one or more of the surgical fastener's openings.

A preferred embodiment of the current invention can be described as a surgical fastener comprising a shank and a head; the shank comprising: a) a length comprising a longitudinal axis traversing from a first end to a second end opposite the first end; the second end comprising a tapered section tapering inward toward the longitudinal axis as the tapered section approaches the second end; b) a conduit extending between the first end and the second end; the conduit adapted to carry one or more biocompatible substances; c) an inward side contiguous with the conduit and an outward side integral with the inward side; d) openings positioned between the first end and the tapered section; each opening extending through the inward and outward sides wherein an outward edge of each opening corresponds to the radius of the outward side such that each opening opens to a surgical environment external of the surgical fastener; e) a thread attached to the outward side and spiraling through a second radius more distant from the longitudinal axis than the outward side's radius, wherein at least two winds of the thread circumscribe each opening; and f) surface treatments for one or more of the head, the shank or the thread.

Another preferred embodiment of the current invention can be described as a surgical fastener comprising: a) a shank comprising: i) a longitudinal axis traversing from a first end to a second end opposite the first end; ii) a conduit extending between the first end and the second end; the conduit adapted to carry one or more biocompatible substances; iii) an inward side contiguous with the conduit and an outward side integral with the inward side; iv) openings positioned between the first end and the second end; each opening extending through the inward and outward sides, wherein an outward edge of each opening corresponds to the radius of the outward side such that each opening opens to a surgical environment external of the surgical fastener; and v) a thread attached to the outward side and turning through a second radius outward from the radius of the outward side, wherein at least a first wind of the thread circumscribes each opening and at least one opening is circumscribed by a second wind of the thread; and b) a head comprising an aperture aligned with the longitudinal axis and a fitting adapted to receive a surgical tool.

Still another preferred embodiment of the current invention can be described as a shank for a surgical fastener; the shank comprising: a) a longitudinal axis traversing from a first end to a second end opposite the first end; b) a conduit extending between the first end and the second end; the conduit adapted to carry one or more biocompatible substances; c) an inward side contiguous with the conduit and an outward side integral with the inward side; d) openings positioned between the first end and the second end; each opening extending through the inward and outward sides, wherein an outward edge of each opening corresponds to the radius of the outward side such that each opening is adapted to dispense biocompatible substances into a surgical environment external of the shank; and e) a thread attached to the outward side and turning through a second radius outward from the radius of the outward side, wherein at least a first wind of the thread circumscribes each opening.

Yet another preferred embodiment of the current invention can be described as a surgical fastener comprising a cannula; the cannula comprising: a) a conduit comprising a first aperture and a second aperture opposite the first aperture; the conduit traversing a longitudinal axis of the cannula and adapted to carry one or more biocompatible substances; b) a wall surrounding the conduit comprising: a first thread zone positioned at a first end of the cannula, a second thread zone positioned at a second end of the cannula and a no thread zone positioned between the first thread zone and the second thread zone, wherein the second thread zone is tapered toward the longitudinal axis as the second thread zone approaches the second aperture; c) openings positioned in the second thread zone; each opening extending from the conduit through the wall such that each opening opens to a surgical environment external of the cannula, wherein an outward edge of each opening corresponds to a first radius; d) a first thread turning about the first thread zone; and e) a second thread positioned in the second thread zone and spiraling through a second radius more distant from the longitudinal axis than the first radius, wherein at least two winds of the thread circumscribe each opening.

Another preferred embodiment of the current invention can be described as a surgical fastener comprising a cannula; the cannula comprising: a) a conduit comprising a first aperture and a second aperture opposite the first aperture; the conduit traversing a longitudinal axis of the cannula and adapted to carry one or more biocompatible substances; b) a wall surrounding the conduit comprising: a first thread zone positioned at a first end of the cannula, a second thread zone positioned at a second end of the cannula and a no thread zone positioned between the first thread zone and the second thread zone, wherein the second thread zone is tapered toward the longitudinal axis as the second thread zone approaches the second aperture; c) openings positioned in the second thread zone; each opening extending from the conduit through the wall such that each opening opens to a surgical environment external of the cannula, wherein an outward edge of each opening corresponds to a first radius; d) a first thread turning about the first thread zone; and e) a second thread positioned in the second thread zone and spiraling through a second radius more distant from the longitudinal axis than the first radius, wherein at least two winds of the thread circumscribe each opening.

Still another preferred embodiment of the current invention can be described as a surgical fastener comprising a cannula; the cannula comprising: a) a conduit adapted to carry one or more biocompatible substances; the conduit traversing a longitudinal axis of the cannula; b) a wall surrounding the conduit; c) openings proximate a lengthwise end of the cannula; each opening extending from the conduit through the wall such that each opening opens to a surgical environment external of the cannula, wherein an outward edge of each opening corresponds to a first radius; and d) a thread positioned in a thread zone and spiraling through a second radius more distant from the longitudinal axis than the first radius such that at least a wind of the thread circumscribes each opening and two winds of the thread circumscribe at least one opening, wherein a section of the thread zone tapers toward the longitudinal axis as the thread zone approaches the second aperture.

It is the novel and unique interaction of these simple elements which creates the apparatus within the ambit of the present invention. Pursuant to the Article 33 of the Patent Cooperation Treaty, descriptions of preferred embodiments follow. However, it is to be understood that the best mode descriptions do not limit the scope of the present invention.

BRIEF DESCRIPTION OF THE DRAWINGS

FIG. 11 is a lateral perspective of another preferred embodiment of fastener (30).

FIG. 11a is a cross-section taken along axis X-X of fastener (30) shown in FIG. 11.

FIG. 12 is a lateral perspective of another preferred embodiment of fastener (30).

FIG. 13 is a lateral perspective of another preferred embodiment of fastener (30).

FIG. 14 is a lateral perspective of another preferred embodiment of fastener (30) provided with no thread zone (206) and thread zone (204) including one or more openings (260).

DESCRIPTION OF THE PREFERRED EMBODIMENTS

Although the disclosure hereof is detailed to enable those skilled in the art to practice the invention, the embodiments published herein merely exemplify the present invention.

In the most general sense, the present invention is a fastener adapted for insertion into bone or any other tissue capable of interlocking with the thread or threads of the fastener. Among other things, the current invention can be adapted for use with vertebra or other bone tissues. The present surgical fastener is particularly adapted for use through the pedicle of a vertebra and in constructs to stabilize fracture bones. The current surgical fastener is provided with a conduit for transporting biocompatible devices/substances, such as adhesives, cameras, cannulas, fiber optics, implants, pharmaceuticals, osteogenics, etc. Dispersion of adhesives from the windows or openings of the surgical fastener before closing the surgical wound, reduces the risk of the fastener backing out of the wound prior to the fastener fully interlocking with tissue overgrowth. Polymethymethacrylate is an adhesive particularly well suited for use with the current fastener. Long term or time released dispersions of pharmaceuticals, osteogenics or other compositions carried by the surgical fastener's conduit subsequent wound closure can assist with the patient's treatment and prognosis.

Preferred embodiments of the present invention are manufactured of titanium alloys, stainless steel, non-resorbable polymers or any other composition acceptable in the art. Within the scope of the present invention, it has advantageously been discovered that shanks or cannulas of the current surgical fastener can have: lengths from about 8 millimeters to about 250 millimeters; diameters from about 1 millimeter to about 30 millimeters; conduit diameters from about 0.2 millimeters to about 15 millimeters; thread pitch of pitch of about 0.1 millimeter to about 10 millimeters; and a tapered section with lengths of from about 0.1 millimeter to about 10 millimeters, a largest diameter of about 20 millimeters and a smallest diameter of about 1 millimeter.

Figure 1:
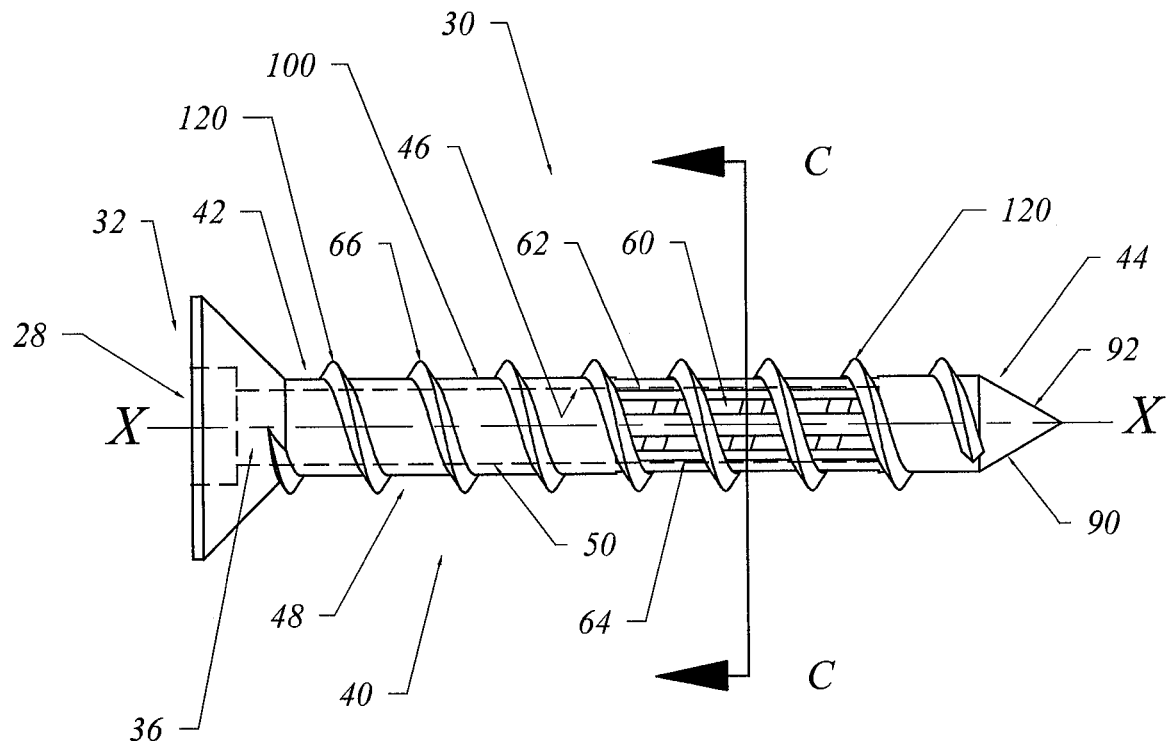
FIG. 1 is lateral perspective of a preferred embodiment of fastener (30).

FIG. 1 is a lateral view of fastener (30). Among other things, in this preferred embodiment, fastener (30) includes head (32) and shank (40) and with tapered section (90). Select preferred embodiments of head (32) include aperture (36) contiguous with conduit (50). Head (32) can be provided with a fitting (28) adapted to contact a surgical tool (not shown). From first end (42) through second end (44) opposite first end (42), axis X-X spans the length of shank (40) and head (32). In this preferred embodiment, conduit (50) surrounds a portion of axis X-X while in other preferred embodiments, conduit (50) can span from first end (42) through second end (44) without circumscribing axis X-X.

Figure 2:
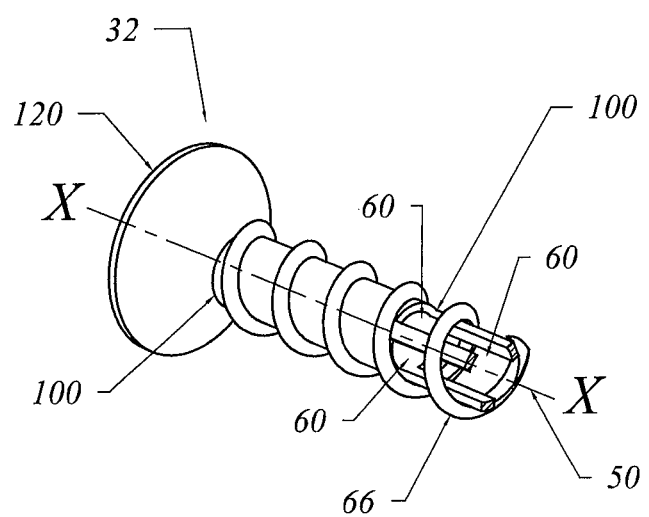
FIG. 2 is a perspective of fastener (30) showing a three dimensional perspective along plane X-X of shank (40), where second end (44) is removed.

FIG. 2 is a perspective of fastener (30) showing a three dimensional perspective along plane X-X of shank (40), where second end (44) is removed. With reference to FIGS. 1 and 2, conduit (50) contacts inward side of (46) and openings (60) of shank (40). As shown in this preferred embodiment, openings (60) have length greater than width. However, openings (60) of any dimensions are compatible with current invention. Inward side (46) of shank (40) is contiguous with conduit (50). Outward side (48) and openings (60) are located about a first radius (100) from axis X-X. In this preferred embodiment, openings (60) are equidistantly spaced from each other. However, in other preferred embodiments, openings (60) can be spaced in other predetermined or random patterns. And still other preferred embodiments of shank (40) have at least two openings (60) positioned on opposite sides of shank (40).

With reference to FIGS. 1-8, one or more threads (66) spiral or turn through a second radius (120) more distant from axis X-X than first radius (100). Preferred embodiments of shanks (40) of the present invention have at least one wind of thread (66) that is continuous along the second radius (120) that circumscribes at least one opening (60). Other preferred embodiments of shanks (40) have at least two winds of thread (66) that circumscribe at least one opening (60). For the purposes of this Application, a thread (66) that "circumscribes" an opening (60) shall mean that the section of the wind circumscribing opening (60) is continuous, without interruption, over and outward of an opening (60) of surgical fastener (30). Applicant believes that surgical fasteners (30) including winds that circumscribe opening (60) can improve surgical fastener's (30) ability to resist movement after surgical fastener (30) is implanted into bone.

Some preferred embodiments of shank (40) are provided with tapered section (90) while other preferred embodiments of the current invention may not utilize a tapered section. As shown, tapered section (90) is tapered toward axis X-X as tapered section approaches tip (92) of tapered section (90). In select preferred embodiments of the current invention, conduit (50) can extend through orifice (54) of tip (92) of tapered section (90).

Figure 3:
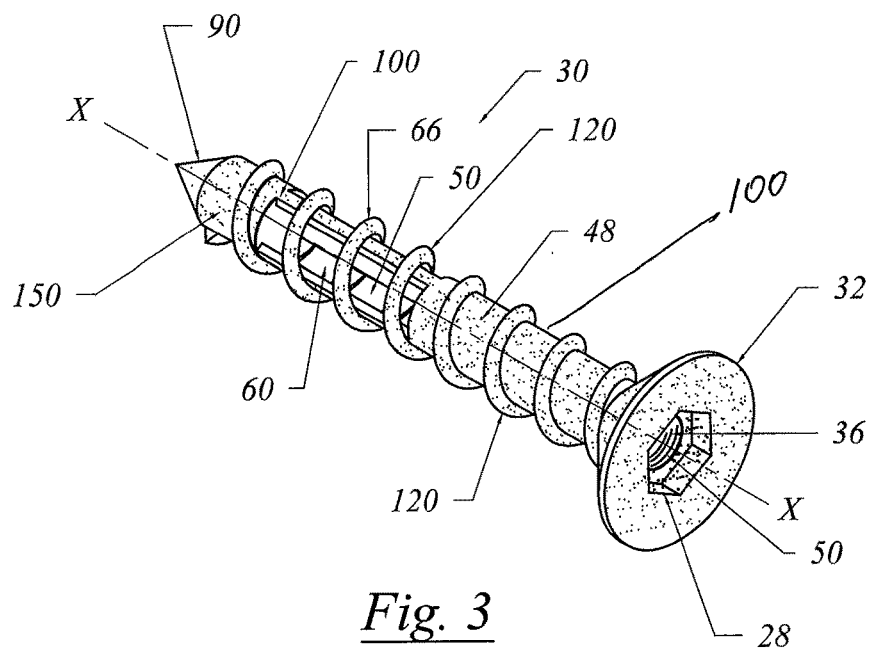
FIG. 3 is a lateral perspective of a preferred embodiment of fastener (30).

FIG. 3 is lateral view of the fastener (30) disclosed in FIG. 1 where one or more surface treatments (150) were applied. Surface treatments (150) can enhance surface area for bone growth. Within the ambit of the current invention, one or more surface treatments (150) can be applied to head (32), outward side (48), conduit (50), thread(s) (66) and tapered section (90). In accordance with the current invention, among other things, surface treatments (150) can include but are not limited to micropores or metal or abrasive particles incorporated into or onto the shank's outward side and thread. Micropores can be created by three dimensional construction methods, abrasive, chemical or laser means.

Figure 4:
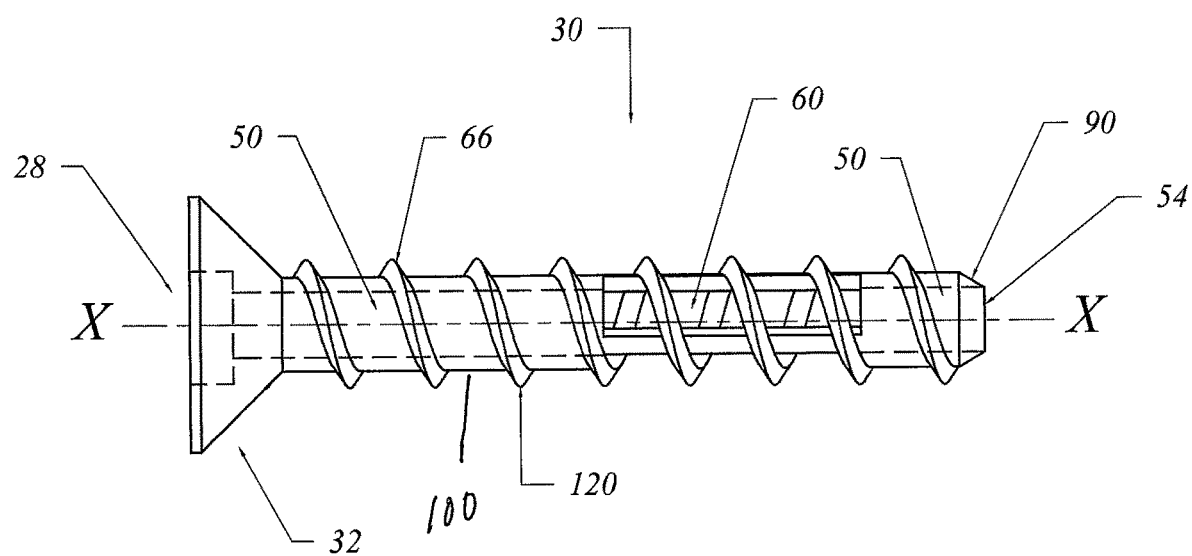
FIG. 4 is a lateral perspective of a preferred embodiment of fastener (30).
Figure 5:
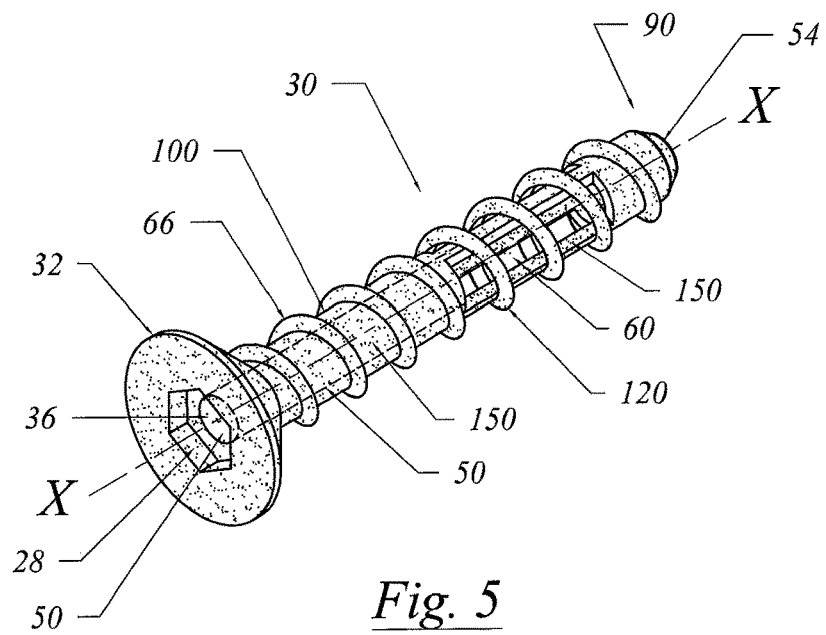
FIG. 5 is a lateral perspective of a preferred embodiment of fastener (30).

With respect to the preferred embodiment of fastener (30) portrayed in FIGS. 4 and 5, conduit (50) spans the entire length of shank (40) to orifice (54) of shank (40).

Figure 6:
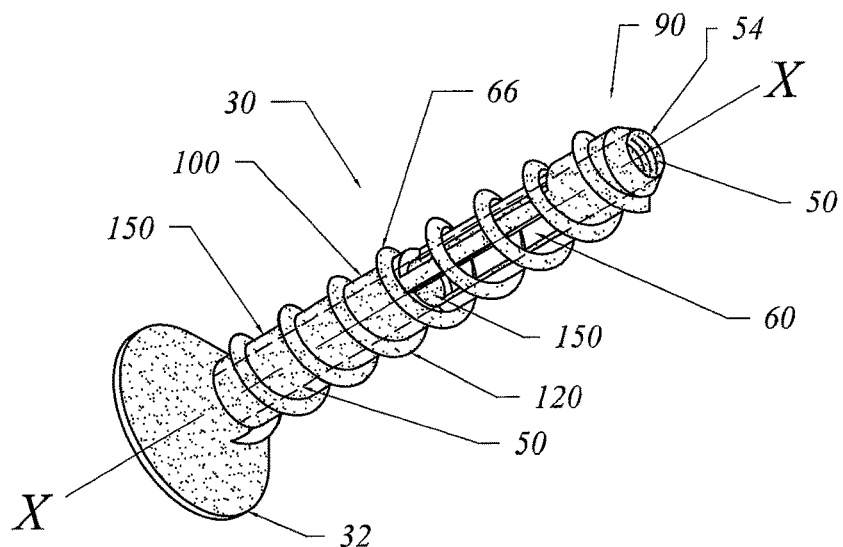
FIG. 6 is a lateral perspective of a preferred embodiment of fastener (30).
Figure 6A:
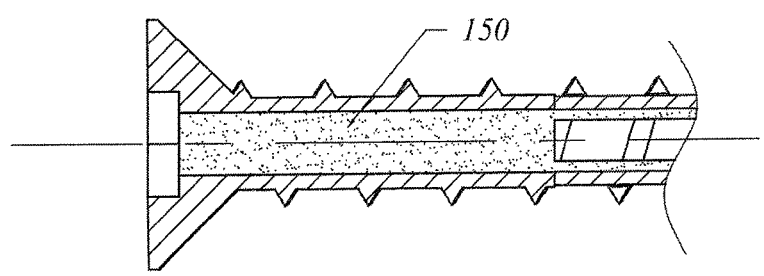
FIG. 6a is a cross-section taken along axis X-X of a portion of fastener (30) shown in FIG. 6.

FIGS. 5 and 6 are representations of preferred embodiments of fastener (30) where one or more of the surface treatments (150) were applied to fastener (30). FIG. 6a is a cross-section taken along axis X-X of a portion of fastener (30) shown in FIG. 6 where surface treatments (150) were applied to conduit (50).

Figure 7:
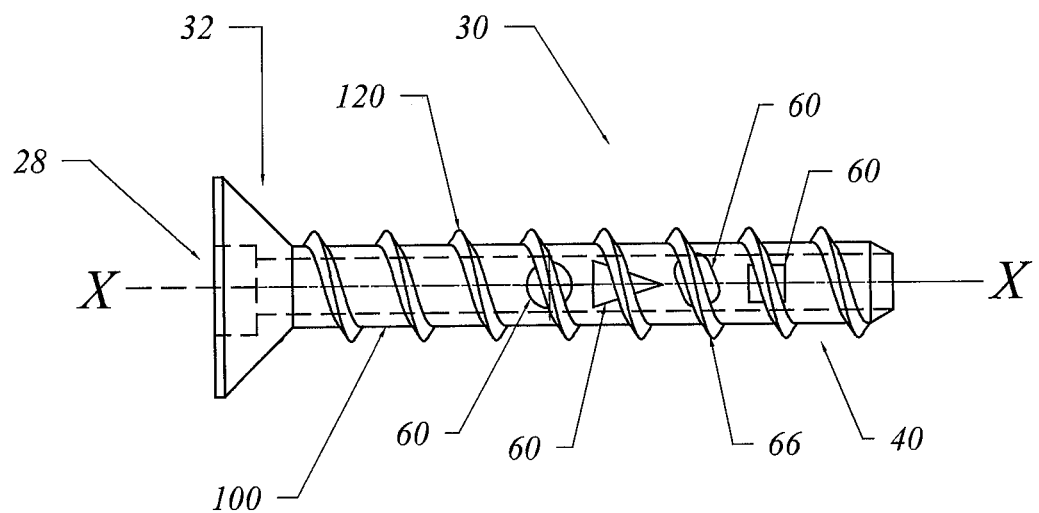
FIG. 7 is a lateral view of a preferred embodiment of the current fastener (30) incorporating openings (60) of different dimensions on shank (40).

FIG. 7 is a lateral view of a preferred embodiment of the current fastener (30) incorporating openings (60) of different dimensions on shank (40).

Figure 8:
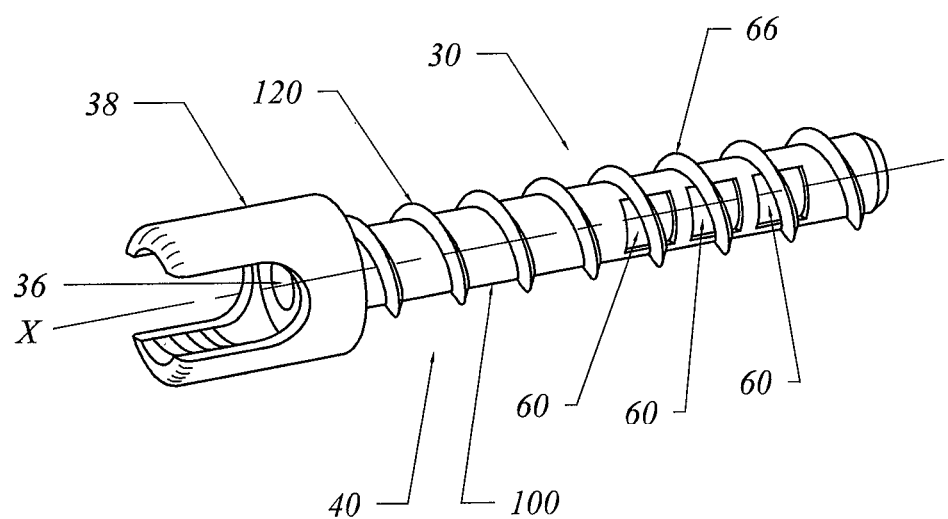
FIG. 8 is a lateral view of a preferred embodiment of the current fastener (30) incorporating a plurality of similarly aligned openings (60) on shank (40).

FIG. 8 is a lateral view of a preferred embodiment of the current fastener (30) incorporating a plurality of similarly aligned openings (60) on shank (40). Within the scope of the current invention, fastener (30) is provided with a polyaxial head (38) and shank (40).

Figure 10:
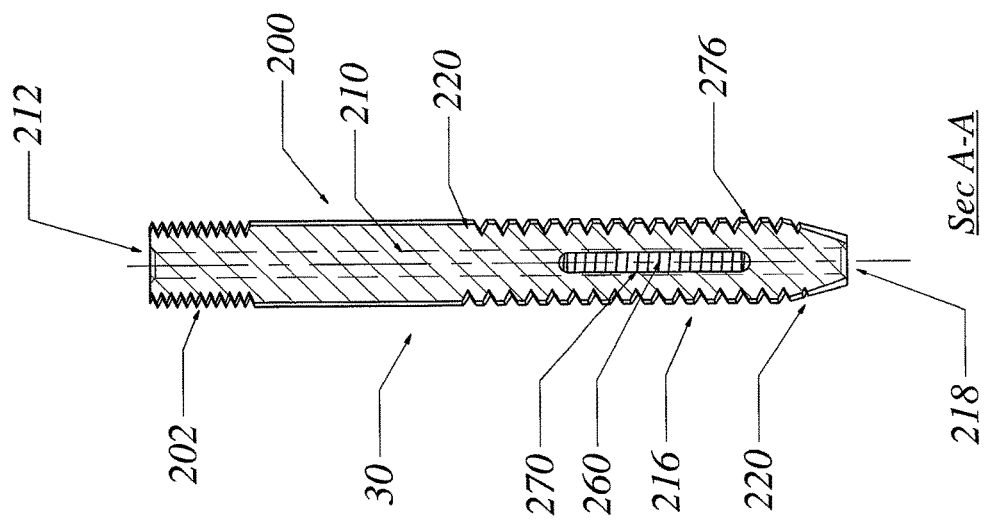
FIG. 10 is a planar cross-sectional view along line A-A of a preferred embodiment of fastener (30) shown in FIG. 9.
Figure 9:
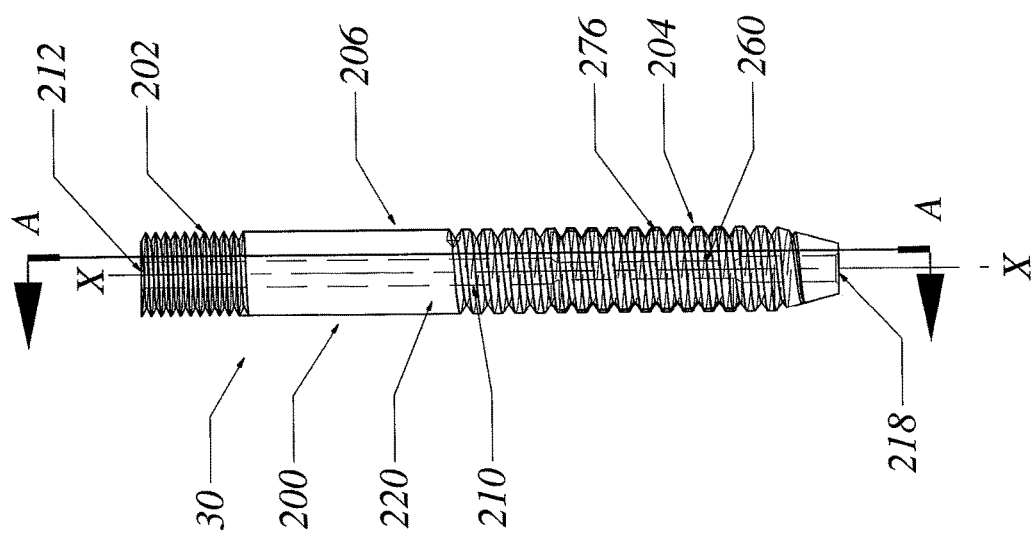
FIG. 9 is a lateral view of a preferred embodiment of fastener (30) that includes cannula (200), conduit (210) and longitudinal axis X-X.

FIG. 9 is a lateral view of fastener (30) that includes cannula (200), conduit (210) and longitudinal axis X-X. FIG. 10 is a cross-sectional view along line A-A of fastener (30) shown in FIG. 9.

With reference to FIGS. 9 and 10, in this preferred embodiment, circular wall (220) of cannula (200) surrounds conduit (210). Wall (220) is provided with first thread zone (202), second thread zone (204) and no thread zone (206) where all zones (202, 204, 206) are associated with the outward side of wall (220). First thread zone (202) includes first aperture (212) that is contiguous with conduit (210) and second thread zone (216) includes second aperture (218) that is contiguous with conduit (210). From first aperture (212) through second aperture (218) opposite first aperture (212), axis X-X spans the length of cannula (200).

First thread zone (202) is adapted to engage a surgical tool (not shown) or a medical device (not shown).

Outward sides of openings (260) positioned in second thread zone (204) are located about a first radius (270) from axis X-X. Second thread zone (204) is provided with thread (276) spiraling through a second radius (280) more distant from longitudinal axis X-X than first radius (270) of one or more openings (260) positioned in wall (220) such that at least a wind of the thread (276) circumscribes each opening (260) and two winds of thread (276) circumscribe at least one opening (260).

In this preferred embodiment, conduit (210) surrounds a portion of axis X-X while in other preferred embodiments, conduit (210) can span from first aperture (212) through second aperture (218) without circumscribing axis X-X. Conduit (210) is shaped by inward side of wall (220).

As shown in this preferred embodiment, openings (260) have length greater than width. However, openings (260) of any dimensions are compatible with current invention. In this preferred embodiment, openings (260) are equidistantly spaced and opposed from each other, but openings (260) can be spaced in other predetermined or random patterns. Openings (260) open to a surgical environment external of cannula (200).

With reference to FIGS. 11-16, one or more threads (276, 276F, 276S) spiral or turn through a second radius (280) more distant from axis X-X than first radius (270). Preferred embodiments of cannulas (200) of the present invention have at least one wind of thread (276S) that is continuous along the second radius (280) such that wind circumscribes at least one opening (260) positioned in the second thread zone (204). Other preferred embodiments of cannulas (200) have at least two winds of thread (276S) that circumscribe at least one opening (260) positioned in the second thread zone (204). In still other preferred embodiments of cannulas (200) thread (276F) and thread (276S) are provided with distinct pitches.

For the purposes of this Application, a thread (276, 275F, 276S) that "circumscribes" an opening (260) shall mean that the section of the wind circumscribing opening (260) is continuous, without interruption, over and outward of an opening (260) of surgical fastener (30). Applicant believes that surgical fasteners (30) including winds that circumscribe opening (60) can improve surgical fastener's (30) ability to resist movement after surgical fastener (30) is implanted into bone.

FIG. 11 is lateral perspective of a preferred embodiment of surgical fastener (30) with surface treatments (150). Surface treatments (150) can enhance surface area for bone growth. Within the ambit of the current invention, one or more surface treatments (150) can be applied to head first thread zone (202), second thread zone (204) or no thread zone (206). Among other things, surface treatments (150) can include but are not limited to micropores or metal or abrasive particles incorporated into or onto the shank's outward side and thread. Micropores can be created by three dimensional construction methods, abrasive, chemical or laser means.

FIG. 11a is a cross-section taken along axis X-X of fastener (30) shown in FIG. 11 where surface treatments (150) were applied to circular wall (220) of cannula (200) surrounding conduit (210).

FIG. 12 is a lateral perspective of another preferred embodiment of fastener (30) where section (222) of the thread zone (204) tapers toward the longitudinal axis as the thread zone (204) approaches the second aperture (218).

FIG. 13 is a lateral perspective of another preferred embodiment of fastener (30) where thread (276F) of first thread zone (202) and second thread (276S) of second thread zone (204) are provided with different pitches.

FIG. 14 is a lateral perspective of another preferred embodiment of fastener (30) provided with no thread zone (206) and thread zone (204) including one or more openings (260).

Figures 15, 16:
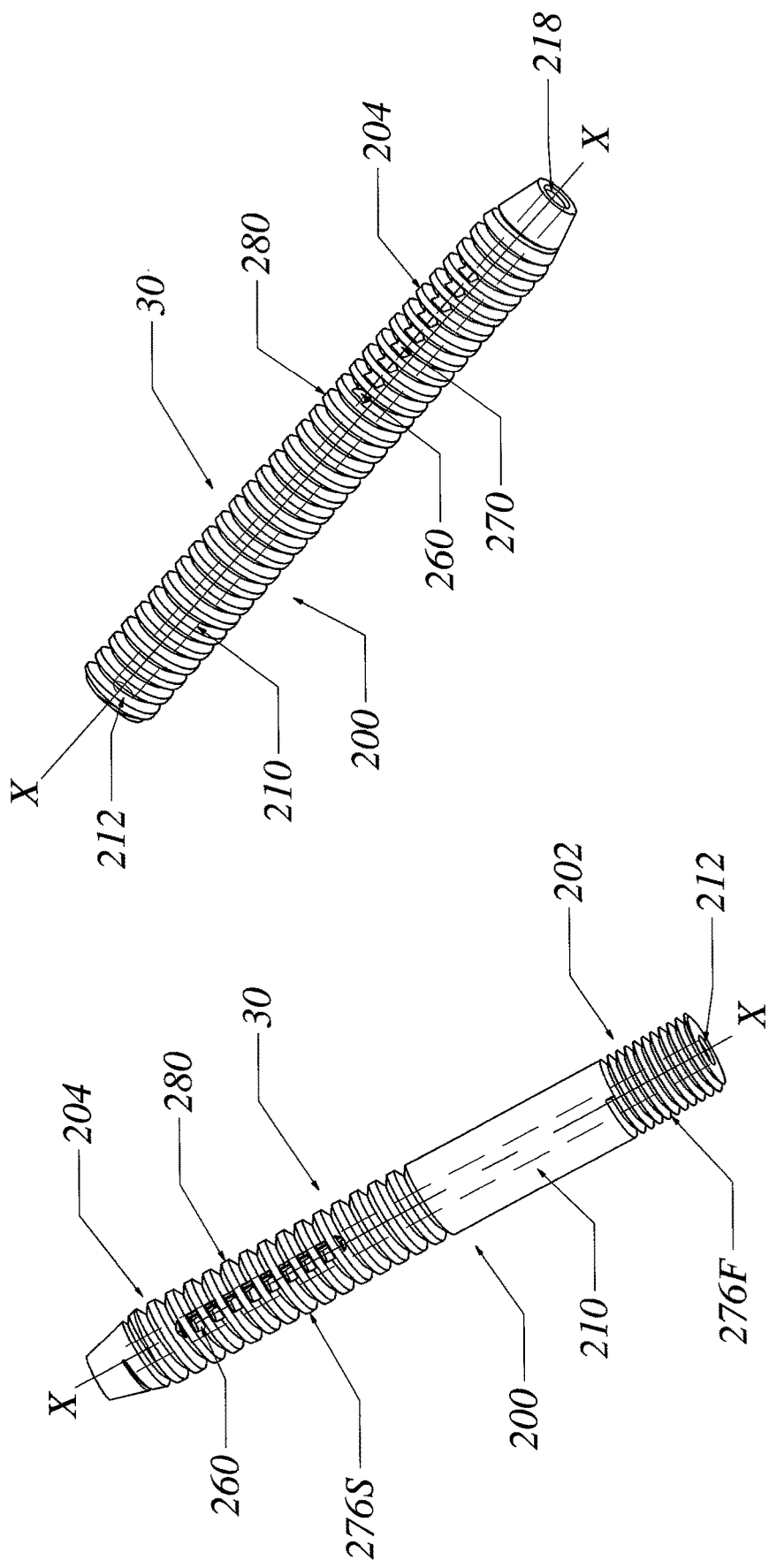
FIG. 15 is a lateral perspective of another preferred embodiment of fastener (30) with thread zone (204) provided with openings (260) on opposite side of thread zone (204).
FIG. 16 is a lateral perspective of another preferred embodiment of fastener (30) showing thread zone (204).

FIG. 15 is a lateral perspective of another preferred embodiment of fastener (30) with thread zone (204) provided with openings (260) on opposite side of thread zone (204).

FIG. 16 is a lateral perspective of another preferred embodiment of fastener (30) showing thread zone (204).

Applicant has enabled, described and disclosed the invention as required by the Patent Cooperation Treaty.

What is claimed is:

1. A surgical fastener comprising a cannula; the cannula comprising:
   a) a conduit adapted to carry one or more biocompatible substances; the conduit traversing an entire length of a longitudinal axis of the surgical fastener;
   b) a cylindrical wall surrounding the conduit comprising a first uninterrupted section proximate a first end and a second interrupted section proximate a second end, wherein the second interrupted section of the continuous cylindrical wall is interrupted by a thread zone comprising one or more openings lateral from the longitudinal axis, wherein the one or more openings do not extend beyond a length of the thread zone;
   c) the one or more openings extending from the conduit through the cylindrical wall such that the one or more openings opens to a surgical environment external of the cannula, wherein an outward edge of each opening corresponds to a first radius; and d) a thread, positioned in the thread zone, outward of the one or more openings spiraling through a second radius more distant from the longitudinal axis than the first radius such that at least a wind of the thread circumscribes each lateral opening and at least two winds of the thread circumscribe at least one lateral opening, wherein a portion of the thread zone tapers toward the longitudinal axis.

2. The surgical fastener of claim 1, wherein:
   a) the openings are equidistant from each other; and
   b) the thread zone comprises surface treatments.

3. The surgical fastener of claim 2, wherein a second thread zone comprises a contact area adapted to engage a surgical tool or a medical device.

4. The surgical fastener of claim 3, wherein a no thread zone comprises surface treatments.

5. The surgical fastener of claim 4, wherein at least two of the openings are on opposite sides of the thread zone and comprise a length greater than a width.

6. The surgical fastener of claim 5, wherein the surface treatments comprise micropores or metal or abrasive particles created by abrasive, chemical or laser applications or three dimensional construction methods.

7. A headless surgical fastener comprising a cannula; the cannula comprising:
   a) a continuous cylindrical wall surrounding a conduit traversing an entire length of the headless surgical fastener; the cylindrical wall comprising:
      i) a first uninterrupted section proximate a first end; and
      ii) a second interrupted section proximate a second end, wherein the second interrupted section of the continuous cylindrical wall is interrupted by a thread zone comprising one or more openings lateral from the longitudinal axis;
   b) the one or more openings extending from the conduit through the cylindrical wall such that each opening opens to a surgical environment external of the cannula, wherein an outward edge of each opening corresponds to a first radius; and
   c) a thread positioned in ft the thread zone outward of the one or more openings spiraling through a second radius more distant from the longitudinal axis than the first radius such that at least a wind of the thread circumscribes each lateral opening and at least two winds of the thread circumscribe at least one lateral opening.

8. The surgical fastener of claim 7, wherein a portion of the thread zone tapers toward the longitudinal axis.

9. The surgical fastener of claim 8, wherein:
   a) the one or more openings are equidistant from each other; and
   b) the thread zone comprises surface treatments.

10. The surgical fastener of claim 9, wherein a lengthwise end of the cannula opposite the tapered thread zone comprises a contact area adapted to engage a surgical tool or a medical device.

11. The surgical fastener of claim 10, wherein at least two of the openings are on opposite sides of the thread zone and comprise a length greater than a width.

12. The surgical fastener of claim 11, wherein the surface treatments comprise micropores or metal or abrasive particles created by abrasive, chemical or laser applications or three dimensional construction methods.

13. A headless cannula comprising:
   a) a cylindrical wall surrounding a conduit traversing an entire length of the headless cannula; the cylindrical wall comprising:
      i) a first uninterrupted section proximate a first end; and
      ii) a second interrupted section comprising a thread zone comprising one or more openings lateral from the longitudinal axis;
   b) the one or more openings extending from the conduit through the cylindrical wall such that each opening opens to a surgical environment external of the cannula, wherein an outward edge of each opening corresponds to a first radius; and
   c) a thread positioned in the thread zone outward of the one or more lateral openings spiraling through a second radius more distant from the longitudinal axis than the first radius such that at least a wind of the thread circumscribes each lateral opening.

14. The headless cannula of claim 13, wherein a portion of the thread zone tapers toward the longitudinal axis.

15. The headless cannula of claim 14, wherein the thread zone comprises surface treatments.

16. The headless cannula of claim 15, wherein:
   a) the openings are equidistant from each other; and
   b) a portion of the first uninterrupted section proximate the first end comprises surface treatments.

17. The headless cannula of claim 16, wherein a lengthwise end of the cannula opposite the thread zone comprises a contact area adapted to engage a surgical tool or a medical device.

18. The headless cannula of claim 7, wherein at least two of the openings are on opposite sides of the thread zone and comprise a length greater than a width.

19. The headless cannula of claim 18, wherein the surface treatments comprise micropores or metal or abrasive particles created by abrasive, chemical or laser applications or three dimensional construction methods.

* * * * *